(12) United States Patent
Guile et al.

(10) Patent No.: US 7,393,854 B2
(45) Date of Patent: Jul. 1, 2008

(54) THIENOPYRIMIDINEDIONES AND THEIR USE IN MODULATION OF AUTOIMMUNE DISEASE

(75) Inventors: Simon David Guile, Loughborough (GB); Anthony Howard Ingall, Loughborough (GB)

(73) Assignee: AstraZeneca AB (SE)

( * ) Notice: Subject to any disclaimer, the term of this patent is extended or adjusted under 35 U.S.C. 154(b) by 0 days.

(21) Appl. No.: 10/542,457

(22) PCT Filed: Jan. 15, 2004

(86) PCT No.: PCT/SE2004/000053

§ 371 (c)(1),
(2), (4) Date: Jul. 14, 2005

(87) PCT Pub. No.: WO2004/065395

PCT Pub. Date: Aug. 5, 2004

(65) Prior Publication Data

US 2006/0135539 A1   Jun. 22, 2006

(30) Foreign Application Priority Data

Jan. 17, 2003  (SE)  .................................. 0300117
Jan. 17, 2003  (SE)  .................................. 0300118

(51) Int. Cl.
*A61K 31/519*  (2006.01)
*C07D 495/04*  (2006.01)
*A61P 11/06*  (2006.01)

(52) U.S. Cl. .................................... 514/260.1; 544/278
(58) Field of Classification Search ................. 544/278; 514/260.1
See application file for complete search history.

(56) References Cited

U.S. PATENT DOCUMENTS

| 6,180,635 B1 | 1/2001 | Cheshire et al. |
| 6,232,320 B1 | 5/2001 | Stewart et al. |
| 6,300,334 B1 | 10/2001 | Bantick et al. |
| 6,342,502 B1 | 1/2002 | Cheshire et al. |
| 7,064,126 B2 | 6/2006 | Cooper et al. |
| 2004/0171623 A1 | 9/2004 | Reynolds et al. |
| 2004/0254198 A1* | 12/2004 | Reynolds et al. ......... 514/260.1 |
| 2006/0052400 A1 | 3/2006 | Guile |

FOREIGN PATENT DOCUMENTS

| WO | WO 98/54190 | 12/1998 |
| WO | WO 99/29695 | 6/1999 |
| WO | WO 00/12514 | 3/2000 |
| WO | WO 03/008422 | 1/2003 |
| WO | WO 03/011868 | 2/2003 |
| WO | WO 2004/065393 | 8/2004 |
| WO | WO 2004/065394 | * 8/2004 |

OTHER PUBLICATIONS

"New Drugs for Asthma, Allergy and COPD," Prog. Respir. Res. Basel, Karger, 2001, vol. 31, pp. 212-216.*
BestHealth entry for ARDS (adult respiratory distress syndrome) <http://www.wfubmc.edu/besthealth/ency/article/000103prv.htm>.*
MDAdvice.com entry for Asthma <http://www.mdadvice.com/topics/asthma/info/1.htm> downloaded from the Internet Mar. 5, 2003.*
AllRefer.com Health entry for Chronic Obstructive Pulmonary Disease <<http://health.allrefer.com/health/chronic-obstructive-pulmonary-disease-prevention.html>> downloaded from the Internet Aug. 23, 2004.*
Yamaguchi et al., "Novel Antiasthmatic Agents with Dual Activities of Thromboxane $A_2$ Synthetase Inhibition and Bronchodilation. V.[1)]Thienopyridazinone Derivatives", *Chem. Pharm. Bull.* 43(2):236-240 (1995).
Gupta et al., "Tacrolimus: a review of its use for the management of dermatoses", *J. Eur. Acad. Dermatol. Venereal.* 16:100-114 (2002).
Meagher et al., "Atopic dermatitis: Review of immunopathogenesis and advances in immunosuppressive therapy", *Australas. J. Derm.* 43:247-254 (2002).
Perrett et al., "Cyclosporin in childhood psoriasis", *Journal of Dermatological Treatment* 14:113-118 (2003).
Tan et al., "Psoriasis", *Drugs of Today* 34(7):641-647 (1998).
Thestrup-Pedersen, "Tacrolimus treatment of atopic eczema/dermatitis syndrome", *Curr Opin Allergy Clin Immunol* 3:359-362 (2003).
Wolff et al., "Pimecrolimus for the treatment of inflammatory skin disease", *Expert Opin. Pharmacother.* 5:643-655 (2004).
Yamamoto et al., "Topical tacrolimus: an effective therapy for facial psoriasis", *Eur J Dermatol* 13:471-473 (2003).
Yu et al., "Refractory atopic dermatitis treated with low dose cyclosporin", *Annals of Allergy, Asthma & Immunology* 89:127-131 (2002).

* cited by examiner

*Primary Examiner*—Brenda L. Coleman
*Assistant Examiner*—Susanna Moore
(74) *Attorney, Agent, or Firm*—Fish & Richardson P.C.

(57) ABSTRACT

The invention relates to thienopyrimidinediones of formula (I):

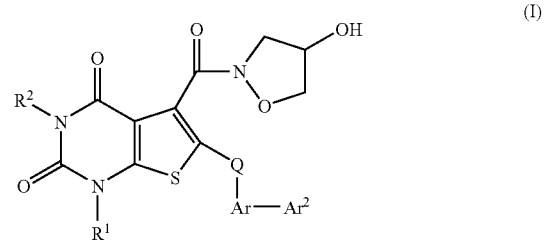

wherein:

$R^1$, $R^2$, Q are as defined in the specification, and Ar and $Ar^2$ are selected from certain aromatic ring systems which may be optionally substituted, as defined in the specification.

Processes for the preparation of compounds of formula (I), pharmaceutical compositions containing them and their use in therapy are also described and claimed.

17 Claims, No Drawings

THIENOPYRIMIDINEDIONES AND THEIR USE IN MODULATION OF AUTOIMMUNE DISEASE

CROSS-REFERENCE TO RELATED APPLICATIONS

This application is the National Stage of International Application No. PCT/SE2004/000053, filed Jan. 15, 2004, which claims the benefit of Swedish Patent Applications Serial No. 0300117-9, filed Jan. 17, 2003 and 0300118-7, filed Jan. 17, 2003. The contents of these applications are hereby incorporated by reference in their entireties.

The present invention relates to thienopyrimidinediones, processes for their preparation, pharmaceutical compositions containing them and their use in therapy. The invention also relates to their use in the modulation of autoimmune disease.

T-cells play an important role in the immune response, however in auto-immune disease T-cells are inappropriately activated against particular tissues and proliferate, eg causing the inflammation associated with rheumatoid arthritis. Inhibition of the proliferation of T-cells is beneficial in the modulation of autoimmune disease. The present invention relates to compounds which are beneficial in the modulation of autoimmune disease.

In accordance with the present invention, there is provided a compound of formula (I):

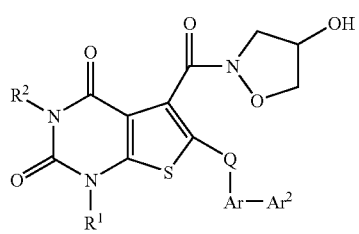

wherein:

$R^1$ and $R^2$ each independently represent $C_{1-6}$alkyl, $C_{3-6}$alkenyl, $C_{3-5}$cycloalkyl$C_{1-3}$alkyl or $C_{3-6}$cycloalkyl, each of which may be optionally substituted by 1 to 3 halogen atoms;

Q is $CR^4R^5$ where $R^4$ is hydrogen, fluorine or $C_{1-6}$ alkyl and $R^5$ is hydrogen, fluorine or hydroxy;

Ar is a 5- to 10-membered aromatic ring system wherein up to 4 ring atoms may be heteroatoms independently selected from nitrogen, oxygen and sulphur, the ring system being optionally substituted by one or more substituents independently selected from $C_{1-4}$alkyl (optionally substituted by 1, 2 or 3 hydroxy groups), $C_{1-4}$alkoxy, halogen, haloalkyl, dihaloalkyl, or trihaloalkyl, (wherein alkyl groups suitably contain from 1 to 4 carbon atoms) $C_{1-4}$alkoxy$C_{1-4}$alkyl, $C_{1-4}$alkylthio, $C_{1-4}$alkoxycarbonyl, $C_{2-4}$alkanoyl, oxo, thioxo, nitro, cyano, —$N(R^6)R^7$ and —$(CH_2)pN(R^8)R^9$, hydroxy, $C_{1-4}$alkylsulphonyl, $C_{1-4}$alkylsulphinyl, carbamoyl, $C_{1-4}$alkylcarbamoyl, di-($C_{1-4}$alkyl) carbamoyl, carboxy, $SO_2N(R^8)R^9$;

$Ar^2$ is a 5 or 6 membered aromatic ring containing up to 4 hetero atoms independently selected from nitrogen, sulphur or oxygen, and which may be optionally substituted by one or more groups independently selected from $C_{1-4}$alkyl (optionally substituted by 1, 2 or 3 hydroxy groups), $C_{1-4}$alkoxy, halogen, haloalkyl, dihaloalkyl, or trihaloalkyl, (wherein alkyl groups suitably contain from 1 to 4 carbon atoms) $C_{1-4}$-alkoxy$C_{1-4}$alkyl, $C_{1-4}$alkylthio, $C_{1-4}$alkoxycarbonyl, $C_{2-4}$alkanoyl, oxo, thioxo, nitro, cyano, —$N(R^6)R^7$ and —$(CH_2)pN(R^8)R^9$, hydroxy, $C_{1-4}$alkylsulphonyl, $C_{1-4}$alkylsulphinyl, carbamoyl, $C_{1-4}$alkylcarbamoyl, di-($C_{1-4}$alkyl)carbamoyl, carboxy, $SO_2N(R^8)R^9$;

p is 1 to 4;

$R^6$ and $R^7$ each independently represent a hydrogen atom, $C_{1-4}$alkanoyl or $C_{1-4}$alkyl group, or together with the nitrogen atom to which they are attached form a 5- to 7-membered saturated heterocyclic ring optionally containing a further O, S, NH or Nalkyl group;

$R^8$ and $R^9$ each independently represent a hydrogen atom, $C_{1-4}$alkanoyl or $C_{1-4}$alkyl group, or together with the nitrogen atom to which they are attached form a 5- to 7-membered saturated heterocyclic ring optionally containing a further O, S, NH or Nalkyl group;

and pharmaceutically acceptable salts and solvates thereof, provided that the compound is other than 5-[(4S)-4-Hydroxyisoxazolidin-2-ylcarbonyl]-1-(isobutyl)-3-methyl-6-[5-methyl-3-phenyl-1H-pyrazol-4-ylmethyl]thieno[2,3-d]pyrimidine-2,4(1H,3H)-dione, 6-[3,5-Dimethyl-1-phenyl-1H-pyrazol-4-ylmethyl]-5-[(4S)-4-hydroxyisoxazolin-2-ylcarbonyl]-1-isobutyl-3-methylthieno[2,3-d]pyrimidine-2,4(1H,3H)-dione or 6-[3,5-Dimethyl-1-phenyl-1H-pyrazol-4-ylmethyl]-5-[(4S)-4-hydroxyisoxazolidin-2-ylcarbonyl]-3-methyl-1-propylthieno[2,3-d]pyrimidine-2,4(1H,3H)-dione or a pharmaceutically acceptable salt or solvate thereof.

Suitably $R^1$ is $C_{1-6}$ alkyl or $C_{3-6}$ cycloalkyl, and in particular $C_{1-6}$ alkyl. More preferably $R^1$ is ethyl, propyl, butyl or cyclopropyl. Most preferably $R^1$ is ethyl, isobutyl, isopropyl or cyclopropyl.

More preferably $R^1$ is $C_{1-4}$ alkyl such as isobutyl or isopropyl.

Preferably $R^2$ is $C_{1-6}$alkyl such as ethyl or methyl, more preferably methyl.

Suitably Q is $CR^5R^6$ where $R^5$ is hydrogen, $C_{1-6}$ alkyl and $R^6$ is hydrogen. Preferably Q is $CR^4R^5$ where $R^4$ and $R^5$ are both hydrogen.

Examples of 5-10 membered mono- or bi-cyclic aromatic ring systems for Ar include thienyl, furanyl, pyrrolyl, pyrrolopyridino, imidazolyl, pyridyl, pyrazinyl, pyrimidyl, pyridazinyl, triazinyl, oxazolyl, thiazolyl, isoxazolyl, pyrazolyl, oxadiazolyl, thiadiazolyl, triazolyl, tetrazolyl and quinolyl.

Examples of 5- to 7-membered saturated heterocyclic rings formed by $R^6$ and $R^7$ and $R^8$ and $R^9$ include morpholine, piperidine, N-alkyl piperidine, piperazine, pyrrolidine and the like. Preferably Ar is a 5 or 6-membered aromatic ring system wherein up to 2 ring atoms may be heteroatoms independently selected from nitrogen, oxygen and sulphur, the ring system being optionally substituted by one or more substituents independently selected from $C_{1-4}$alkyl, $C_{1-4}$alkoxy, halogen, halo$C_{1-4}$alkyl, dihalo$C_{1-4}$alkyl, tri halo$C_{1-4}$alkyl, oxo, thioxo, cyano, or $C_{1-4}$alkylsulphonyl.

More preferably Ar is 5-membered aromatic ring containing two nitrogen atoms and substituted as above.

A particular example of Ar is an optionally substituted pyrazole ring. Preferably Ar is a substituted pyrazole ring.

Most preferably Ar is a pyrazole ring di-substituted by $C_{1-4}$alkyl, especially methyl.

For instance, Ar is suitably a group of sub-formula (i)

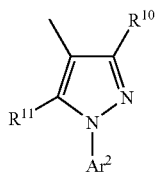

(i)

where $R^{10}$ and $R^{11}$ are independently selected from H, $C_{1-6}$alkyl, halo$C_{1-4}$alkyl, dihalo$C_{1-4}$alkyl, or trihalo$C_{1-4}$alkyl, and $Ar^2$ is as defined above.

In $R^{10}$ and $R^{11}$ are selected from H or $C_{1-3}$alkyl, such as methyl. In particular, both $R^{10}$ and $R^{11}$ is $C_{1-3}$alkyl such as methyl.

$Ar^2$ is suitably a 5 or 6-membered aromatic ring system wherein up to 3 ring atoms may be heteroatoms independently selected from nitrogen, oxygen and sulphur, the ring system being optionally substituted by one or more substituents independently selected from $C_{1-4}$alkyl, $C_{1-4}$alkoxy, halogen, dihaloalkyl, trihaloalkyl, oxo, thioxo, cyano, $C_{1-4}$alkylsulphonyl.

Preferably $Ar^2$ is other than phenyl. In particular $Ar^2$ includes at least one heteroatom.

Examples of haloalkyl groups are halo$C_{1-4}$alkyl groups which include halomethyl groups such as fluoroethyl groups. Examples of dihaloalkyl groups are dihalo$C_{1-4}$alkyl groups including difluoromethyl and dichloromethyl. Examples of trihaloalkyl groups are trihalo$C_{1-4}$alkyl groups such as trifluoromethyl.

In a preferred embodiment, $Ar^2$ is 5-membered aromatic ring containing a nitrogen and sulphur atom and substituted as above. Most preferably $Ar^2$ is a thiazole ring substituted by halogen, especially fluoro.

In an alternative embodiment of the invention, $Ar^2$ is pyridine or pyrimidine. The rings carry at least one substituent, but are preferably unsubstituted.

Preferably $Ar^2$ is pyridinyl or pyrimidinyl.

Preferred compounds of formula (I) include:
6-[[3,5-dimethyl-1-(2-pyrimidinyl)-1H-pyrazol-4-yl]methyl]-5-[[(4S)-4-hydroxy-2-isoxazolidinyl]carbonyl]-3-methyl-1-(1-methylethyl)thieno[2,3-d]pyrimidine-2,4(1H,3H)-dione, and
6-[[3,5-dimethyl-1-(2-pyridinyl)-1H-pyrazol-4-yl]methyl]-5-[[(4S)-4-hydroxy-2-isoxazolidinyl]carbonyl]-3-methyl-1-(1-methylethyl)thieno[2,3-d]pyrimidine-2,4(1H,3H)-dione, and pharmaceutically acceptable salts thereof.

Other preferred compounds of formula (I) include (S)-2-[[6-[[3,5-Dimethyl-1-(2-thiazolyl)-1H-pyrazol-4-yl]methyl]-1,2,3,4-tetrahydro-3-methyl-1-(1-methylethyl)-2,4-dioxothieno[2,3-d]pyrimidin-5-yl]carbonyl]4 isoxazolidinol and pharmaceutically acceptable salts thereof.

Alkyl groups, whether alone or as part of another group, can be straight chained or branched. Unless otherwise stated, they may contain from 1 to 6, and preferably from 1 to 4 carbon atoms.

It will be understood that a compound of the formula (I) or a salt thereof may exhibit the phenomenon of tautomerism and that the drawings within this specification represent only one of the possible tautomeric forms. It is to be understood that the invention encompasses any tautomeric form.

Certain compounds of formula (I) are capable of existing in stereoisomeric forms. It will be understood that the invention encompasses all geometric and optical isomers of the compounds of formula (I) and mixtures thereof including racemates. These also form an aspect of the present invention.

Salts for use in pharmaceutical compositions will be pharmaceutically acceptable salts, but other salts may be useful in the production of the compounds of formula I and their pharmaceutically acceptable salts. Pharmaceutically acceptable salts of the invention may, for example, include acid addition salts of the compounds of formula I as hereinbefore defined which are sufficiently basic to form such salts. Such acid addition salts include for example salts with inorganic or organic acids affording pharmaceutically acceptable anions such as with hydrogen halides (especially hydrochloric or hydrobromic acid of which hydrochloric acid is particularly preferred) or with sulphuric or phosphoric acid, or with trifluoroacetic, citric or maleic acid. Suitable salts include hydrochlorides, hydrobromides, phosphates, sulphates, hydrogen sulphates, alkylsulphonates, arylsulphonates, acetates, benzoates, citrates, maleates, fumarates, succinates, lactates and tartrates. In addition where the compounds of formula I are sufficiently acidic, pharmaceutically acceptable salts may be formed with an inorganic or organic base which affords a pharmaceutically acceptable cation. Such salts with inorganic or organic bases include for example an alkali metal salt, such as a sodium or potassium salt, an alkaline earth metal salt such as a calcium or magnesium salt, an ammonium salt or for example a salt with methylamine, dimethylamine, trimethylamine, piperidine, morpholine or tris-(2-hydroxyethyl)amine.

Preferred salts include an acid addition salt such as a hydrochloride, hydrobromide, phosphate, acetate, fumarate, maleate, tartrate, citrate, oxalate, methanesulfonate or p-toluenesulfonate, or an alkali metal salt such as a sodium or potassium salt.

In a further aspect the invention provides a process for the preparation of a compound of formula (I) which comprises:

(a) Reaction of a compound of formula (II):

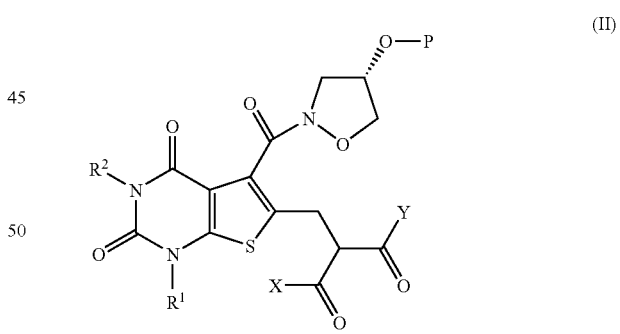

(II)

in which $R^1$ and $R^2$ are as defined in formula (I) or are protected derivatives thereof, and X and Y are selected from $C_{1-4}$alkyl (optionally substituted by 1, 2 or 3 hydroxy groups), $C_{1-4}$alkoxy, haloalkyl, dihaloalkyl, trihaloalkyl, $C_{1-4}$alkoxy$C_{1-4}$alkyl, $C_{1-4}$alkoxycarbonyl, —(CH$_2$)pN(R$^8$)R$^9$, with a compound of formula (III):

(III)

where $Ar^2$ is as defined in formula (I) or are protected derivatives thereof and G1 is NH, G2 is $N_2$, SH or OH, or (b) Reacting a compound of formula (IV):

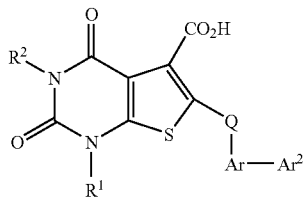

in which $R^1$, $R^2$, Ar and $Ar^2$ are as defined in formula (I) or are protected derivatives thereof, with a compound of formula (V)

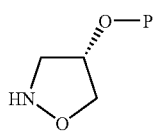

in which P is a protecting group, or (c) For compounds of formula (I) where Ar has an NH group, reacting a compound of formula (VI):

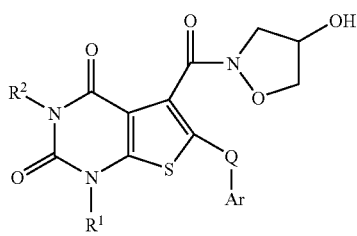

in which $R^1$ and $R^2$ and as defined in formula (I) and Ar is as defined in formula (I) provided Ar has an NH group, or are protected derivatives thereof, with a compound of formula (VII):

$Ar^2-L$ (VII)

in which $Ar^2$ is as defined in formula (I) or is a protected derivative thereof and L is a leaving group,
and optionally thereafter process (a), (b) or (c) in any order
removing any protecting groups
forming a pharmaceutically acceptable salt.

Reaction of compounds (II) and (III) is suitably carried out in an inert solvent eg ethanol, at a temperature of from 0° C. to 100° C., preferably 10° C. to 50° C., optionally in the presence of a catalytic quantity of an acid eg trifluoroacetic acid.

Reaction of compounds (IV) and (V) is carried out by conversion of the carboxylic acid function to an activated form by reaction with a coupling agent eg EDCI and 1-hydroxybenzotriazole, in an inert solvent eg dichloromethane, in the presence of a base, preferably triethylamine or ethyldiisopropylamine, at a temperature of from 0° C. to 100° C., preferably 10° C. to 50° C., in the presence of compound (V).

Reaction of compounds (VI) and (VII) is carried out either by heating in an inert solvent such as NMP in the presence of a base, for example a metal carbonate, under microwave irradiation; or by use of catalytic (or stoicheiometric) Buchwald conditionsusing a Cu(I) salt with a diamine ligand in a solvent such as dioxan at a temperature of about 100° C. The group L is any suitable leaving group, preferably L is halogen.

Compounds of formula (II) can be prepared by reacting a compound of formula (VIII):

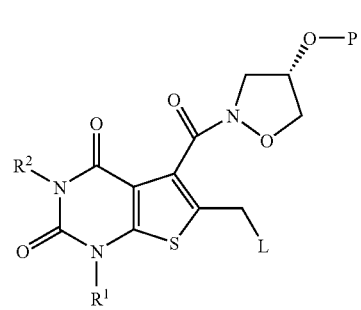

in which $R^1$, $R^2$ and P are as defined above and L is a leaving group with a nucleophilic fragment of a the group Ar such as a zinc salt of a beta-diketone. L is preferably a halogen such as bromo.

Compounds of formula (VIII) can be prepared from compounds of formula (IX):

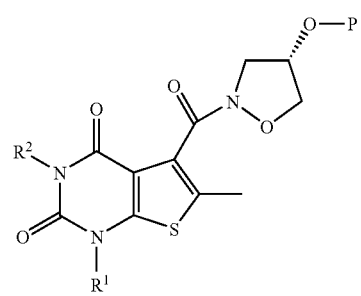

in which $R^1$, $R^2$ and P are as defined above by, for example, bromination using N-bromosuccinamide in an inert solvent such as chloroform under a light source at a temperature of from 15° C. to 80° C., preferably at 50° C. to 70° C.

Compounds of formula (IX) can be prepared by protection of the corresponding alcohols of formula (X):

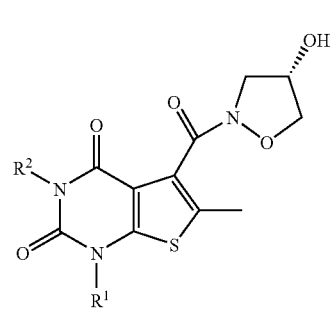

in which $R^1$, $R^2$ and P are as defined above by, for example, reacting with a trialkylsilyl halide in an inert solvent such as dichloromethane at a temperature of from 0° C. to 60° C., preferably 10° C. to 30° C., in the presence of a base such as imidazole.

Compounds of formula (X) can be prepared from acids of formula (XI):

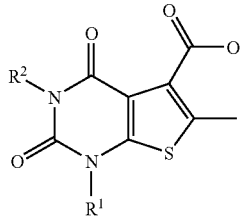

(XI)

in which $R^1$, $R^2$ and P are as defined above by forming an acid chloride by treating with a reagent such as oxalyl chloride in an inert solvent such as dichloromethane at a temperature of from 0° C. to 60° C., preferably 10° C. to 30° C., followed by treatment of the resulting acid chloride with the hydroxy-isooxazolidine in a solvent such as dichloromethane at a temperature of from 0° C. to 60° C., preferably 10° C. to 30° C. in the presence of a base such as triethylamine.

Compounds of formula (XI) are prepared from the corresponding esters using standard conditions.

Compounds of formula (IV) can be prepared from compounds of formula (XII):

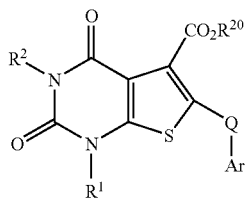

(XII)

in which $R^1$, $R^2$ and Ar are as defined above, provided that Ar contains an NH group, and $R^{20}$ is an ester forming group by, for example, reacting with a compound of formula (XIII)

 Ar²-halogen (XIII)

in which $Ar^2$ is as defined above or by reaction with a compound $Ar^2$ where Ar is as defined above provided that Ar contains a nitrogen centre.

Reaction of compounds (XII) and (XIII) can be carried out in an inert solvent such as dioxan at a temperature of 10° C. to 120° C. in the presence of a copper (I) salt and an alkylene diamine. The group $R^{20}$ is an ester forming group such as alkyl, especially methyl.

Reaction of compounds (XII) and $Ar^2$ can be carried out in a solvent such as dimethyl acetamide at a temperature of 10° C. to 200° C. in the presence of a base such as potassium carbonate optionally with microwave irradiation.

A compound of formula (XII) can be prepared from a compound of formula (XV):

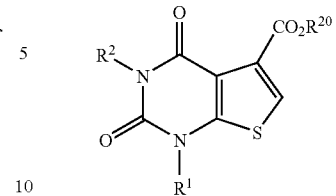

(XV)

in which $R^1$, $R^2$ and $R^{20}$ are as defined above by reaction with a strong base such as lithium diisopropylamide in a solvent such as THF at −78° C. to 0° C. followed by the addition of a compound of formula (XVI):

 Ar—CHO (XVI)

Compounds of formula (IV) are prepared from compounds of formula (XVII):

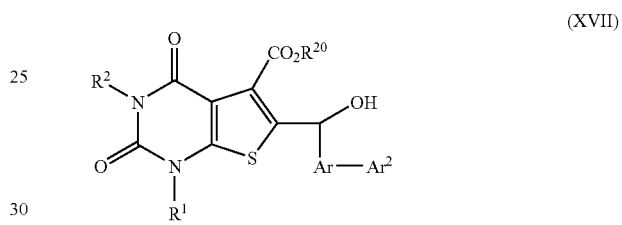

(XVII)

in which $R^1$, $R^2$, $R^{20}$, Ar and $Ar^2$ are as defined above, either by deoxygenation using a strong acid such as TFA in the presence of a hydride source such as triethylsilane, optionally in a solvent such as dichloromethane at a temperature of 10° C. to 40° C., or by activation of the hydroxyl group by esterification with an activated carboxylic acid such as trifluoroacetic anhydride or methane sulphonyl chloride in an inert solvent such as ethyl acetate followed by hydrogenolysis, for example using palladium on carbon at 1 to 5 bar at 10° C. to 80° C.

Compounds of formula (XVII) are prepared from compounds of formula (XV) as defined above by reacxting with compounds (XVIII):

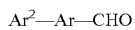 Ar²—Ar—CHO (VIII)

in which Ar and $Ar^2$ are as ddefined above using conditions analogous to those above for the reaction of compounds (XV) and (XVI).

Compounds of formula (VI) may be made from compounds of formula (XII) by hydrolysis of the ester function (using an alkali metal or alkaline earth hydroxide in a solvent containing water eg aqueous ethanol or aqueous methanol) at a temperature of from 0° C. to 100° C., or using aqueous mineral acid in an inert solvent at a temperature of from 20° C. to 100° C., and then coupling the acid residue with a compound of formula (V) in the presence of a condensing agent eg PyBrOP in an inert solvent eg THF in the presence of a base such as triethylamine at a temperature of from 0° C. to 30° C.

Starting materials as defined above are available commercially or can be prepared using routine chemistry known in the art.

The compounds of the invention are useful because they possess pharmacological activity in human and non-human animals. They are indicated as pharmaceuticals for use in the (prophylactic) treatment of autoimmune, inflammatory, proliferative and hyperproliferative diseases and immunologically mediated diseases including rejection of transplanted organs or tissues and Acquired Immunodeficiency Syndrome (AIDS).

Examples of these conditions are:
(1) (the respiratory tract) airways diseases including chronic obstructive pulmonary disease (COPD); asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;
(2) (bone and joints) rheumatoid arthritis, seronegative spondyloarthropathies (including ankylosing spondylitis, psoriatic arthritis and Reiter's disease), Behcet's disease, Sjogren's syndrome and systemic sclerosis;
(3) (skin) psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia greata and vernal conjunctivitis;
(4) (gastrointestinal tract) Coeliac disease, proctitis, eosinopilic gastro-enteritis, mastocytosis, Crohn's disease, ulcerative colitis, food-related allergies which have effects remote from the gut, e.g., migraine, rhinitis and eczema;
(5) (other tissues and systemic disease) multiple sclerosis, atherosclerosis, Acquired Immunodeficiency Syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia pupura;
(6) (allograft rejection) acute and chronic following, for example, transplantation of kidney, heart, liver, lung, bone marrow, skin and cornea; and chronic graft versus host disease; and
(7) cancer.

Accordingly, the present invention provides a compound of formula (I) or a pharmaceutically acceptable salt thereof as hereinbefore defined for use in therapy.

In another aspect, the invention provides the use of a compound of formula (I) or a pharmaceutically acceptable salt thereof as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention further provides a method of effecting immunosuppression (e.g. in the treatment of allograft rejection) which comprises administering to a patient a therapeutically effective amount of a compound of formula (I) or a pharmaceutically acceptable salt thereof as hereinbefore defined.

The invention still further provides a method of treating, or reducing the risk of, an airways disease (e.g. asthma or COPD) in a patient suffering from, or at risk of, said disease, which comprises administering to the patient a therapeutically effective amount of a compound of formula (I) or a pharmaceutically-acceptable salt thereof as hereinbefore defined.

For the above-mentioned therapeutic uses the dosage administered will, of course, vary with the compound employed, the mode of administration, the treatment desired and the disorder indicated. However, in general, for effecting immunosuppression, the daily dosage of the compound of formula (I) will be in the range from 0.1 mg/kg, preferably from 0.3 mg/kg, more preferably from 0.5 mg/kg and still more preferably from 1mg/kg up to and including 30 mg/kg. For the treatment of airways diseases, the daily dosage of the compound of formula (I) will typically be in the range from 0.001 mg/kg to 30 mg/kg.

The compounds of formula (I) and pharmaceutically-acceptable salts thereof may be used on their own but will generally be administered in the form of a pharmaceutical composition in which the formula (I) compound/salt/solvate (active ingredient) is in association with a pharmaceutically-acceptable adjuvant, diluent or carrier. Depending on the mode of administration, the pharmaceutical composition will preferably comprise from 0.05 to 99% w (per cent by weight), more preferably less than 80% w, e.g. from 0.10 to 70% w, and even more preferably less than 50% w, of active ingredient, all percentages by weight being based on total composition.

Thus, the present invention also provides a pharmaceutical composition comprising a compound of formula (I) or a pharmaceutically acceptable salt thereof as hereinbefore defined, in association with a pharmaceutically acceptable adjuvant, diluent or carrier.

The invention further provides a process for the preparation of a pharmaceutical composition of the invention which comprises mixing a compound of formula (I) or a pharmaceutically acceptable salt thereof as hereinbefore defined, with a pharmaceutically acceptable adjuvant, diluent or carrier.

The pharmaceutical composition of the invention may be administered topically (e.g. to the lung and/or airways or to the skin) in the form of solutions, suspensions, heptafluoroalkane aerosols and dry powder formulations; or systemically, e.g. by oral, administration in the form of tablets, capsules, syrups, powders or granules, or by parenteral administration in the form of solutions or suspensions, or by subcutaneous administration or by rectal administration in the form of suppositories or transdermally.

The ability of compounds which can inhibit PMA/ionomycin-stimulated peripheral blood mononuclear cell proliferation can be assessed, for example using the procedure set out below.

The invention will now be illustrated in the following Examples in which, unless otherwise stated:
(i) evaporations were carried out by rotary evaporation in vacuo and work-up procedures were carried out after removal of residual solids such as drying agents by filtration;

(ii) operations were carried out at ambient temperature, that is in the range 18-25° C. and under an atmosphere of an inert gas such as argon or nitrogen;
(iii) yields are given for illustration only and are not necessarily the maximum attainable;
(iv) the structures of the end-products of the formula I were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;
(v) intermediates were not generally fully characterised and purity was assessed by thin layer chromatography (TLC), high-performance liquid chromatography (HPLC), mass spectrometry (MS), infra-red (IR) or NMR analysis;

Abbreviations
2,3-Dichloro-5,6-dicyano-1,4-benzoquinone DDQ
Dimethylformamide DMF
Tetrahydrofuran THF The following examples illustrate the invention.

EXAMPLE 1

6-[[3,5-dimethyl-1-(2-pyrimidinyl)-1H-pyrazol-4-yl]methyl]-5-[[(4S)-4-hydroxy-2-isoxazolidinyl]carbonyl]-3-methyl-1-(1-methylethyl)thieno[2,3-d]pyrimidine-2,4(1H,3H)-dione

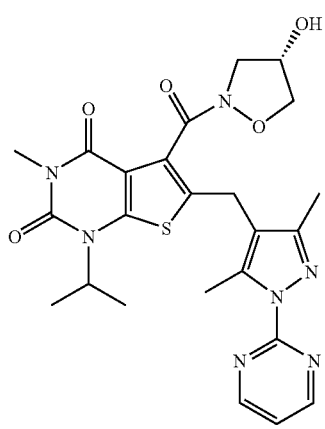

a) Ethyl methyl 2-methyl-5-(N,N-methylethylamino)-thiophene-3,4-dicarboxylate

Ethoxycarbonylmethylene triphenyl phosphorane (33.8 g) in dry THF (200 ml) was treated with isopropyl isothiocyanate (10.1 g) at 65° C. for 16 h under nitrogen. The mixture was cooled to −78° C. and methyl 3-bromo-2-oxo-butanoate was added. The reaction was allowed to warm slowly to room temperature. After 24 h at room temperature more methyl 3-bromo-2-oxo-butanoate (2.8 g) was added and the mixture was warmed to 60° C. for 16 h. The cooled reaction was poured into water (1.5 L) and extracted into ether. Drying and evaporation gave an oil which was chromatographed (SiO$_2$/10:1 isohexane-ethyl acetate then 5:1 isohexane-ethyl acetate) to afford the sub-title compound (23.5 g).

δ $^1H_{CDCl_3}$ 1.23-1.35 (9H, m), 2.26 (3H,s), 3.46 (1H, m), 3.82 (3H, s), 4.2 (2H, q), 7.42 (1H, br.s)

b) Methyl 1,2,3,4-tetrahydro-3,6-dimethyl-1-(1-methylethyl)-2,4-dioxo-thieno[2,3-d]pyrimidine-5-carboxylate Silver cyanate (13.5 g) suspended in anhydrous toluene (90 ml) under nitrogen was treated dropwise with acetyl chloride (5.34 ml) and stirred vigorously for 30 min. The product of step a) (23 g) dissolved in anhydrous toluene (15 ml) was added and the mixture was stirred for 72 h. Ether (360 ml) was added and the insoluble material was filtered off and washed with a small volume of ether. The combined organic solutions were washed with saturated sodium bicarbonate solution, dried and evaporated. The residue was treated with a solution of sodium methoxide in methanol (25 wt %, 64 ml) at room temperature for 72 h. The reaction was cooled in ice and treated with trimethylsilyl chloride (50.8 ml) and stirred at room temperature overnight. All volatiles were removed in vacuo and the residue partitioned between water and ethyl acetate. Drying and evaporation of the organic solution left a residue, which was chromatographed (SiO$_2$/2:1 isohexane-ethyl acetate then 3:2 isohexane-ethyl acetate) to isolate the major component (12.2 g). This was taken in dry DMF (150 ml) with potassium carbonate (6.95 g) and methyl iodide (7.1 g) for 72 h at room temperature. The mixture was poured into water (2 L), acidified and extracted into ether. Washing with brine, drying and evaporation gave a solid which was boiled in isohexane (200 ml) containing ethyl acetate (3 ml). On cooling the precipitated pale yellow solid was collected and dried, to afford the sub-title compound (10.5 g).

MS (APCI) [M+H]$^+$ 297

δ $^1H_{CDCl_3}$ 1.6 (6H, d), 2.44 (3H, s), 3.37 (3H, s), 3.95 (3H, s), 4.66 (1H, br)

c) 1,2,3,4-Tetrahydro-3,6-dimethyl-1-(1-methylethyl)-2,4-dioxo-thieno[2,3-d]pyrimidine-5-carboxylic acid To a solution of the product of step b) (3.81 g) in THF (50 ml) and methanol (5 ml) was added 1N NaOH (25.7 ml) and the mixture stirred under nitrogen for 18 hr. It was acidified with 2.5N HCl and extracted with DCM, the organic extracts washed with water, dried over anhydrous magnesium sulfate, filtered and evaporated under reduced pressure to give the sub-title compound as a solid (3.40 g)

MS (ESI) 283 [M+H]$^+$ d) 5-[[(4S)-4-Hydroxy-2-isoxazolidinyl]carbonyl]-3,6-dimethyl-1-(1-methylethyl)thieno[2,3-d]pyrimidine-2,4(1H,3H)-dione To a suspension of the product of part c) (3.40 g) in DCM (50 ml) was added oxalyl chloride (1.16 ml) and DMF (10 μl) and the mixture stirred under nitrogen for 2 hr. The acid chloride solution was added to a suspension of (S)-4-isoxazolidinol hydrochloride (1.51 g) and triethylamine (3.52 ml) in DCM (20 ml) at 0° C. under nitrogen and the mixture stirred at room temperature for 3 hr. It was washed with water, dried over anhydrous magnesium sulfate, filtered and evaporated under reduced pressure. The residue was purified by column chromatography over silica, eluting with ethyl acetate to give the sub-title compound as a solid (2.52 g).

MS (ESI) 354 [M+H]$^+$

δ $^1H_{DMSO}$ 1.50-1.52 (6H, m), 2.30-2.34 (3H, m), 3.18-3.19 (3H, m), 3.42-4.08 (4H, m), 4.59-4.74 (2H, m), 5.49-5.50 (1H, m)

e) 5-[[(4S)-4-[[(1,1-Dimethylethyl)dimethylsilyl]oxy]-2-isoxazolidinyl]carbonyl]-3,6-dimethyl-1-(1-methylethyl)thieno[2,3-d]pyrimidine-2,4(1H,3H)-dione To a solution of the product of part d) (2.52 g) in DCM (30 ml) was added imidazole (0.53 g) and tert-butyldimethylsilyl chloride (1.18 g) and the mixture stirred under nitrogen for 24 hr. It was acidified with 1N HCl and extracted with DCM, the organic extracts washed with water, dried over anhydrous magnesium sulfate, filtered and evaporated under reduced pressure. The residue was purified by column chromatography over silica, eluting with i-hexane/ethyl acetate (3:1) followed by i-hexane/ethyl acetate (1:1) to give the sub-title compound (2.42 g).

δ $^1$H$_{DMSO}$ 0.09 (6H, d), 0.86 (9H, s), 1.50 (6H, d), 2.31-2.34 (3H, m), 3.18-3.19 (3H, m), 3.44-4.15 (4H, m), 4.50-4.97 (2H, m)

f) 6-Bromomethyl-5-[[(4S)-4-[[(1,1-dimethylethyl)dimethylsilyl]oxy]-2-isoxazolidinyl]carbonyl]-3-methyl-1-(1-methylethyl)thieno[2,3-d]pyrimidine-2,4(1H,3H)-dione to a solution of the product of part e) (2.42 g) in chloroform (100 ml) was added N-bromosuccinimide (1.01 g) and the mixture heated under reflux whilst being irradiated with a 300 W tungsten lamp for 2 hr. It was cooled, washed with 1N NaOH solution, washed with water, dried over anhydrous magnesium sulfate, filtered and evaporated under reduced pressure to give the sub-title compound (2.83 g)

MS (ESI) 546 and 548 [M+H]$^+$ g) 6-(2-Acetyl-3-oxobutyl)-5-[[(4S)-4-[[(1,1-dimethylethyl)dimethylsilyl]oxy]-2-isoxazolidinyl]carbonyl]-3-methyl-1-(1-methylethyl)thieno[2,3-d]pyrimidine-2,4(1H,3H)-dione A solution of the product of part f) (2.83 g) and zinc acetylacetonate hydrate (1.47 g) in chloroform (50 ml) was heated under reflux for 1 hr. It was cooled, washed with sodium bicarbonate solution, filtered through celite, washed with brine, dried over anhydrous magnesium sulfate, filtered and evaporated under reduced pressure to give the sub-title compound (2.93 g)

MS (ESI) 566 [M+H]$^+$ h) 5-[[(4S)-4-[[(1,1-Dimethylethyl)dimethylsilyl]oxy]-2-isoxazolidinyl]carbonyl]-6-[[3,5-dimethyl-1-(2-pyrimidinyl)-1H-pyrazol-4-yl]methyl]-3-methyl-1-(1-methylethyl)thieno[2,3-d]pyrimidine-2,4(1H,3H)-dione To a solution of the product of part g) (0.73 g) in chloroform (25 ml) was added pyrimidin-2-ylhydrazine (0.27 g) and the mixture stirred for 48 hr. It was washed with water, dried over anhydrous magnesium sulfate, filtered and evaporated under reduced pressure. The residue was purified by column chromatography over silica, eluting with i-hexane/ethyl acetate (1:1) followed by i-hexane/ethyl acetate (1:4) to give the sub-title compound (0.43 g).

MS (ESI) 640 [M+H]$^+$ i) 6-[[3,5-Dimethyl-1-(2-pyrimidinyl)-1H-pyrazol-4-yl]methyl]-5-[[(4S)-4-hydroxy-2-isoxazolidinyl]carbonyl]-3-methyl-1-(1-methylethyl)thieno[2,3-d]pyrimidine-2,4(1H,3H)-dione A solution of the product of part h) (0.43 g) and trifluoroacetic acid (0.5 ml) in DCM (10 ml) was stirred for 72 hr. It was concentrated in vacuo, diluted with sodium bicarbonate solution, and extracted with ethyl acetate, the organic extracts washed with water, dried over anhydrous magnesium sulfate, filtered and evaporated under reduced pressure. The residue was purified by column chromatography over silica, eluting with ethyl acetate then ethyl acetate/methanol (9:1) to give the title compound (30 mg).

MS (APCI) 526 [M+H]$^+$

δ $^1$H$_{DMSO}$ 1.44-1.46 (6H, m), 2.16-2.19 (3H, m), 2.53-2.55 (3H, m), 3.17-3.19 (3H, m), 3.48-4.14 (6H, m), 4.38 (1H, s, br), 4.60-4.80 (1H, m), 5.48-5.52 (1H, m), 7.46 (1H, dt), 8.87 (2H, t)

EXAMPLE 2

6-[[3,5-dimethyl-1-(2-pyridinyl)-1H-pyrazol-4-yl]methyl]-5-[[(4S)-4-hydroxy-2-isoxazolidinyl]carbonyl]-3-methyl-1-(1-methylethyl)thieno[2,3-d]pyrimidine-2,4(1H,3H)-dione

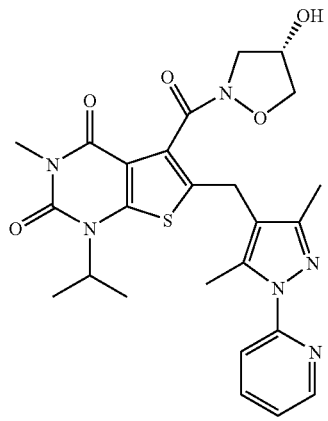

a) 5-[[(4S)-4-[[(1,1-Dimethylethyl)dimethylsilyl]oxy]-2-isoxazolidinyl]carbonyl]-6-[[3,5-dimethyl-1-(2-pyridinyl)-1H-pyrazol-4-yl]methyl]-3-methyl-1-(1-methylethyl)thieno[2,3-d]pyrimidine-2,4(1H,3H)-dione To a solution of the product of example 1 part g) (0.73 g) in chloroform (25 ml) was added pyridin-2-ylhydrazine (0.28 g) and the mixture stirred for 48 hr. It was washed with water, dried over anhydrous magnesium sulfate, filtered and evaporated under reduced pressure. The residue was purified by column chromatography over silica, eluting with i-hexane followed by i-hexane/ethyl acetate (1:1) to give the sub-title compound (0.28 g).

MS (ESI) 639 [M+H]$^+$ b) 6-[[3,5-Dimethyl-1-(2-pyridinyl)-1H-pyrazol-4-yl]methyl]-5-[[(4S)-4-hyroxy-2-isoxazolidinyl]carbonyl]-3-methyl-1-(1-methylethyl)thieno[2,3-d]pyrimidine-2,4(1H,3H)-dione A solution of the product of part a) (0.28 g) and trifluoroacetic acid (0.5 ml) in DCM (10 ml) was stirred for 72 hr. It was concentrated in vacuo, diluted with sodium bicarbonate solution, and extracted with ethyl acetate, the organic extracts washed with water, dried over anhydrous magnesium sulfate, filtered and evaporated under reduced pressure. The residue was purified by column chromatography over silica, eluting with ethyl acetate then ethyl acetate/methanol (49:1) to give the title compound (88 mg).

MS (APCI) 525 [M+H]$^+$

δ $^1$H$_{DMSO}$ 1.44-1.47 (6H, m), 2.17-2.19 (3H, m), 2.56-2.58 (3H, m), 3.47-4.14 (6H, m), 4.38 (1H, s, br), 4.60-4.80 (1H, m), 5.51-5.52 (1H, m), 7.30-7.34 (1H, m), 7.80 (1H, d), 7.95 (1H, dt), 8.45-8.47 (1H, m)

EXAMPLE 3

(S)-2-[[6-[[3,5-Dimethyl-1-(2-thiazolyl)-1H-pyrazol-4-yl]methyl]-1,2,3,4-tetrahydro-3-methyl-1-(1-methylethyl)-2,4-dioxothieno[2,3-d]pyrimidin-5-yl]carbonyl]-4-isoxazolidinol

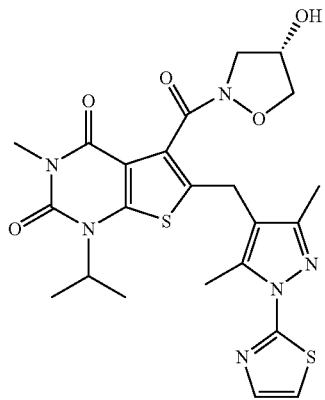

A mixture of (S)-2-[[6-[(3,5-methyl-1H-pyrazol-4-yl)methyl]-1,2,3,4-tetrahydro-3-methyl-1-(1-methylethyl)-2,4-dioxothieno[2,3-d]pyrimidin-5-yl]carbonyl]-4-isoxazolidinol (237 mg), 2-bromothiazole (237 mg), copper(I) iodide (20 mg), trans-cyclohexane-1,2-diamine (15 mg) and potassium carbonate (145 mg) were heated at 100° C. in 1,4-dioxane (1 ml) for 24 hrs. The reaction mixture was concentrated to dryness and purified by chromatography on SiO2 (Biotage cartridge) (eluting with EtOAc to 5% MeOH in EtOAc) and subsequently reverse phase chromatography to give the title compound as a white solid (110 mg).

MS (APCI+ve) M+H=531.1

δ $^1$H$_{DMSO}$, 120° C. 1.47 (6H, d), 2.17 (3H, s), 2.60 (3H, s), 3.20 (3H, s), 3.46(1H, d), 3.75(1H, d), 3.89-3.95 (2H, m), 3.89 (2H, s), 4.46 (1H, sep), 4.70 (1H, s), 5.08 (1H, s), 7.38 (1H, d), 7.56 (1H, d).

Pharmacological Data

Inhibition of PMA/Ionomycin-Stimulated Peripheral Blood Mononuclear Cell Proliferation The assay for PMA/ionomycin-stimulated PBMC proliferation was performed in 96-well flat-bottomed microtitre plates. Compounds were prepared as 10 mM stock solutions in dimethyl sulfoxide. A 50-fold dilution of this was prepared in RPMI and serial dilutions were prepared from this solution 10 μl of the 50-fold diluted stock, or dilutions of it, were added to the well to give concentrations in the assay starting at 9.5 μM and going down. Into each well was placed 1×10$^5$ PBMC, prepared from human peripheral blood from a single donor, in RPMI1640 medium supplemented with 10% human serum, 2 mM glutamine and penicillin/streptomycin. Phorbol myristate acetate (PMA) (0.5 ng/ml final concentration) and ionomycin (500 ng/ml final concentration) were added to these cells in supplemented RPMI1640 medium (as above) so that the final volume of the assay was 0.2 ml. The cells were incubated at 37° C. in a humidified atmosphere at 5% carbon dioxide for 72 hours. $^3$H-Thymidine (0.5 μCi) was added for the final 6 hours of the incubation. The level of radioactivity incorporated by the cells was then determined and this is a measure of proliferation.

The compounds of the Examples were found to exhibit an IA$_{50}$ value of less than 1×10$^{-6}$ M in the above test. Of the specific examples, examples 1 had a PIA$_{50}$ of 8.3 and Example 3 had a PIA$_{50}$ of 9.07 in the above test.

The invention claimed is:

1. A compound of formula (I):

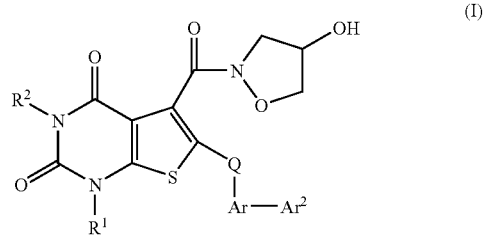

wherein:

R$^1$ and R$^2$ each independently represent C$_{1-6}$alkyl, C$_{3-6}$alkenyl, C$_{3-5}$cycloalkylC$_{1-3}$alkyl or C$_{3-6}$cycloalkyl, each of which may be optionally substituted by 1 to 3 halogen atoms;

Q is CR$^4$R$^5$ where R$^4$ is hydrogen, fluorine or C$_{1-6}$ alkyl and R$^5$ is hydrogen, fluorine or hydroxy;

Ar is a 5- to 10-membered aromatic ring system wherein up to 4 ring atoms are optionally heteroatoms independently selected from nitrogen, oxygen and sulphur, the ring system being optionally substituted by one or more substituents independently selected from C$_{1-4}$alkyl (optionally substituted by 1, 2 or 3 hydroxy groups), C$_{1-4}$alkoxy, halogen, haloalkyl, dihaloalkyl, or trihaloalkyl (wherein alkyl groups suitably contain from 1 to 4 carbon atoms), C$_{1-4}$alkoxyC$_{1-4}$alkyl, C$_{1-4}$alkylthio, C$_{1-4}$alkoxycarbonyl, C$_{2-4}$alkanoyl, nitro, cyano, —N(R$^6$)R$^7$ and —(CH$_2$)pN(R$^8$)R$^9$, hydroxy, C$_{1-4}$alkylsulphonyl, C$_{1-4}$alkylsulphinyl, carbamoyl, C$_{1-4}$alkylcarbamoyl, di-(C$_{1-4}$alkyl)carbamoyl, carboxy, SO$_2$N(R$^8$)R$^9$;

Ar$^2$ is a 5 or 6 membered aromatic ring containing up to 4 heteroatoms independently selected from nitrogen, sulphur or oxygen, and which may be optionally substituted by one or more groups independently selected from C$_{1-4}$alkyl (optionally substituted by 1,2 or 3 hydroxy groups), C$_{1-4}$alkoxy, halogen, haloalkyl, dihaloalkyl, or trihaloalkyl, (wherein alkyl groups suitably contain from 1 to 4 carbon atoms) C$_{1-4}$alkoxyC$_{1-4}$alkyl, C$_{1-4}$alkylthio, C$_{1-4}$alkoxycarbonyl, C$_{2-4}$alkanoyl, nitro, cyano, —N(R$^6$)R$^7$ and —(CH$_2$)pN(R$^8$)R$^9$, hydroxy, C$_{1-4}$alkylsulphonyl, C$_{1-4}$alkylsulphinyl, carbamoyl, C$_{1-4}$alkylcarbamoyl, di-(C$_{1-4}$alkyl)carbamoyl, carboxy, SO$_2$N(R$^8$)R$^9$;

p is 1 to 4;

R$^6$ and R$^7$ each independently represent a hydrogen atom, C$_{1-4}$alkanoyl or C$_{1-4}$alkyl group, or together with the nitrogen atom to which they are attached form a 5- to 7-membered saturated heterocyclic ring optionally containing a further O, S, NH or N-alkyl group;

$R^8$ and $R^9$ each independently represent a hydrogen atom, $C_{1-4}$alkanoyl or $C_{1-4}$alkyl group, or together with the nitrogen atom to which they are attached form a 5- to 7-membered saturated heterocyclic ring optionally containing a further O, S, NH or N-alkvl group;

or a pharmaceutically acceptable salt thereof, provided that the compound is other than 5-[(4S)-4-Hydroxyisoxazolidin-2-ylcarbonyl]-1-(isobutyl)-3-methyl-6-[5-methyl-3-phenyl-1H-pyrazol-4-ylmethyl]thieno[2,3-d]pyrimidine-2,4(1H,3H)-dione, 6-[[3,5-Dimethyl-1-phenyl-1H-pyrazol-4-yl]methyl]-5-[(4S)-4-hydroxyisoxazolidin-2-ylcarbonyl]-1-isobutyl-3-methylthieno[2,3-d]pyrimidine-2,4(1H,3H)-dione or 6-[[3,5-Dimethyl-1-phenyl-1H-pyrazol-4-yl]methyl]-5-[(4S)-4-hydroxyisoxazolidin-2-ylcarbonyl]-3-methyl-1-propylthieno[2,3-d]pyrimidine-2,4(1H,3H)-dione or a pharmaceutically acceptable salt thereof.

2. A compound according to claim 1 in which $R^1$ is $C_{1-6}$alkyl.

3. A compound according to claim 1 in which $R^2$ is methyl.

4. A compound according to claim 1 in which Q is $CH_2$.

5. A compound according to claim 1 in which Ar is a 5 or 6-membered aromatic ring system wherein up to 2 ring atoms are optionally heteroatoms independently selected from nitrogen, oxygen and sulphur, the ring system being optionally substituted by one or more substituents independently selected from $C_{1-4}$alkyl, $C_{1-4}$alkoxy, halogen, haloalkyl, dihaloalkyl, trihaloalkyl, cyano and $C_{1-4}$alkylsulphonyl.

6. A compound according to claim 5 wherein Ar is a group of sub-formula (i)

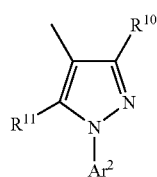

(i)

where $R^{10}$ and $R^{11}$ are independently selected from H, $C_{1-4}$alkyl, or halo$C_{1-4}$alkyl and $Ar^2$ is as defined above.

7. A compound according to claim 1 wherein $Ar^2$ is other than phenyl.

8. A compound according to claim 7 wherein $Ar^2$ contains at least one heteroatom.

9. A compound according to claim 1 in which $Ar^2$ is a 5 or 6-membered aromatic ring system wherein up to 3 ring atoms are optionally heteroatoms independently selected from nitrogen, oxygen and sulphur, the ring system being optionally substituted by one or more substituents independently selected from $C_{1-4}$alkyl, $C_{1-4}$alkoxy, halogen, dihaloalkyl, trihaloalkyl, cyano and $C_{1-4}$alkylsulphonyl.

10. A compound according to claim 9 wherein $Ar^2$ is pyridinyl or pyrimidinyl.

11. A compound according to claim 9 wherein $Ar^2$ is thiazolyl.

12. A compound according to claim 1 selected from:
(S)-2-[[6-[[3,5-Dimethyl-1-(2-thiazolyl)-1H-pyrazol-4-yl]methyl]-1,2,3,4-tetrahydro-3-methyl-1-(1-methylethyl)-2,4-dioxothieno[2,3-d]pyrimidin-5-yl]carbonyl]-4-isoxazolidinol
and pharmaceutically acceptable salts thereof.

13. A pharmaceutical composition comprising a compound of formula (I) or a pharmaceutically acceptable salt thereof as defined in claim 1 and a pharmaceutical carrier.

14. A method of treating asthma in a patient suffering from asthma, which comprises administering to the patient a therapeutically effective amount of a compound of formula (I) or a pharmaceutically-acceptable salt thereof as defined in claim 1.

15. A process for the preparation of a compound of formula (I) according to claim 1 which comprises:

(a) reaction of a compound of formula (II):

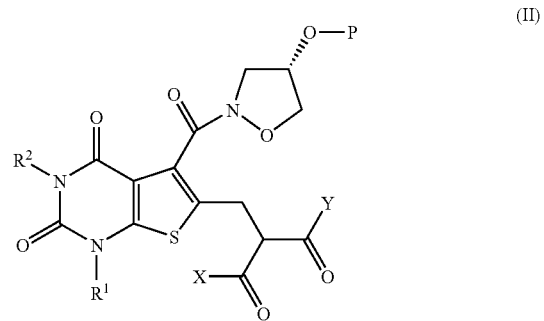

(II)

in which $R^1$ and $R^2$ are as defined in formula (I) or are protected derivatives thereof, and X and Y are selected from $C_{1-4}$alkyl (optionally substituted by 1,2 or 3 hydroxy groups), $C_{1-4}$alkoxy, haloalkyl, dihaloalkyl, trihaloalkyl, $C_{1-4}$alkoxy$C_{1-4}$alkyl, $C_{1-4}$alkoxycarbonyl, $-(CH_2)pN(R^8)R^9$, with a compound of formula (III):

$Ar^2$-G1-G2 (III)

where $Ar^2$ is as defined in formula (I) or are protected derivatives thereof and G1 is NH, G2 is $NH_2$, SH or OH, or (b) reacting a compound of formula (IV):

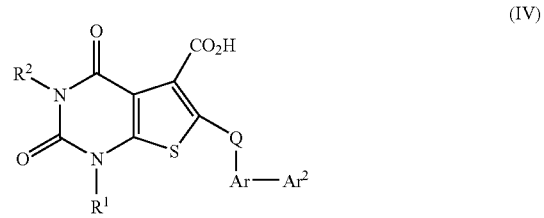

(IV)

in which $R^1$, $R^2$, Ar and $Ar^2$ are as defined in formula (I) or are protected derivatives thereof, with a compound of formula (V)

(V)

in which P is a protecting group, or (c) for compounds of formula (I) where Ar has an NH group, reacting a compound of formula (VI):

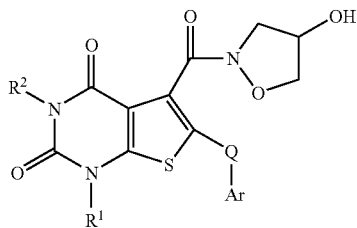

in which R¹ and R² are as defined in formula (I) and Ar is as defined in formula (I) provided Ar has an NH group, or are protected derivatives thereof, with a compound of formula (VII):

in which Ar² is as defined in formula (I) or is a protected derivative thereof and L is a leaving group, and optionally thereafter process (a), (b) or (c) in any order removing any protecting groups, forming a pharmaceutically acceptable salt.

16. A compound according to claim 1, wherein the compound is:

6-[[3,5-dimethyl-1-(2-pyrimidinyl)-1H-pyrazol-4-yl]methyl]-5-[[(4S)-4-hydroxy-2-isoxazolidinyl]carbonyl]-3-methyl-1-(1-methylethyl)thieno[2,3-d]pyrimidine-2,4(1H,3H)-dione or a pharmaceutically acceptable salt thereof.

17. A compound according to claim 1, wherein the compound is:

6-[[3,5-dimethyl-1-(2-pyridinyl)-1H-pyrazol-4-yl]methyl]-5-[[(4S)-4-hydroxy-2-isoxazolidinyl]carbonyl]-3-methyl-1-(1-methylethyl)thieno[2,3-d]pyrimidine-2,4(1H,3H)-dione or a pharmaceutically acceptable salt thereof.

* * * * *

UNITED STATES PATENT AND TRADEMARK OFFICE
CERTIFICATE OF CORRECTION

PATENT NO. : 7,393,854 B2  Page 1 of 1
APPLICATION NO. : 10/542457
DATED : July 1, 2008
INVENTOR(S) : Simon David Guile It is certified that error appears in the above-identified patent and that said Letters Patent is hereby corrected as shown below:

Title Page, Column 1 Item (54)

Line 1, delete "THIENOPYRIMIDINEDINONES" insert
-- THIENOPYRIMIDINEDIONES --

Column 1 (Title)

Line 1, delete "THIENOPYRIMIDINEDINONES" insert
-- THIENOPYRIMIDINEDIONES --

Column 17

Line 5, delete "alkvl" insert -- alkyl --

Column 17

Line 67, after "Claim 1" insert -- , --

Signed and Sealed this

Sixteenth Day of September, 2008

JON W. DUDAS
*Director of the United States Patent and Trademark Office*

UNITED STATES PATENT AND TRADEMARK OFFICE
CERTIFICATE OF CORRECTION

PATENT NO. : 7,393,854 B2  Page 1 of 1
APPLICATION NO. : 10/542457
DATED : July 1, 2008
INVENTOR(S) : Simon David Guile It is certified that error appears in the above-identified patent and that said Letters Patent is hereby corrected as shown below:

Title Page, Left Column

Immediately before "Appl. No.: 10/542,457", insert --This patent is subject to a terminal disclaimer.--

Signed and Sealed this

Seventeenth Day of February, 2009

JOHN DOLL
*Acting Director of the United States Patent and Trademark Office*